United States Patent [19]

Olthoff et al.

[11] Patent Number: 5,085,869
[45] Date of Patent: Feb. 4, 1992

[54] PHARMACEUTICAL GRANULATE

[75] Inventors: Margaretha Olthoff, Rijswijk; Bernardus L. J. Dijkgraaf, Delft; Piet J. Akkerboom, Zoetermeer, all of Netherlands

[73] Assignee: Gist-Brocades N.V., Delft, Netherlands

[21] Appl. No.: 315,268

[22] Filed: Feb. 24, 1989

[30] Foreign Application Priority Data

Feb. 25, 1988 [EP] European Pat. Off. ............ 88200346

[51] Int. Cl.$^5$ .................. A61K 9/16; A61K 33/06
[52] U.S. Cl. .................... 424/499; 424/494; 424/686; 424/692; 514/819
[58] Field of Search ............... 424/494, 464, 499, 465, 424/686, 691, 692; 514/819

[56] References Cited

U.S. PATENT DOCUMENTS

| | | | |
|---|---|---|---|
| 4,292,299 | 9/1981 | Suzuki et al. | 424/16 |
| 4,454,108 | 6/1984 | Iida et al. | 424/16 |
| 4,665,081 | 5/1987 | Doi et al. | 514/356 |
| 4,753,801 | 6/1988 | Oren et al. | 424/465 |
| 4,777,033 | 10/1988 | Ikura, et al. | 424/44 |
| 4,837,030 | 6/1989 | Valorose, Jr. et al. | 424/456 |

FOREIGN PATENT DOCUMENTS

| | | |
|---|---|---|
| 0049061 | 4/1982 | European Pat. Off. |
| 0080862 | 8/1983 | European Pat. Off. |
| 0159735 | 10/1985 | European Pat. Off. |
| 0281200 | 9/1988 | European Pat. Off. |
| 2058565 | 4/1981 | United Kingdom |
| 2172006 | 9/1986 | United Kingdom |

OTHER PUBLICATIONS

The Merck Index, 10th Ed., (1983), p. 810, reference no. 5478, "Magnesium Carbonate Hydroxide".

*Primary Examiner*—Thurman K. Page
*Assistant Examiner*—Amy Hulina
*Attorney, Agent, or Firm*—Fleit, Jacobson, Cohn, Price, Holman & Stern

[57] ABSTRACT

A wet granulate is provided for therapeutically useful substances having a water solubility 10 wt % or less and microcrystalline or microfine cellulose or a mixture of both, where substantial amounts of wet binders are avoided.

Tableting mixtures with the new granulate possess a good flow pattern and may be compressed to tablets which show an excellent disintegration behavior.

15 Claims, No Drawings

PHARMACEUTICAL GRANULATE

The invention relates to a pharmaceutical granulate having improved flow properties from which tablets of improved disintegration behaviour and other dosage forms can be obtained.

BACKGROUND OF THE INVENTION

The action of drugs is based on the presence of an active principle, a therapeutically useful substance. As a rule, the active principle should be mixed with other substances, which may be therapeutically active itself or are needed as adjuvants for the manufacture of a proper dosage form. With pharmaceutical operations in which powders are involved, it is important that the powder has good flow properties. Many therapeutically useful compounds, however, cannot easily be processed to dosage forms, particularly tablets or capsules, because they have an inherent unsatisfactory flow behaviour. Therefore, according to well established pharmaceutical practice, before tableting, those substances are first converted into a granulate which possesses the desired flow properties. The present invention involves wet granulation, where the active principle is mixed with a granulation liquid, which often is water and where special granulation adjuvants may be added. According to well known procedures, a wet mass is passed through a sieve grit, dried, milled and sieved. The thus resulting granulate may be used e.g. as ingredient in a tableting mixture, but when capsules are chosen as the dosage form the granulate can be used as such.

In order to lend the granules a solid consistency, according to standard practice, a wet binding substance (wet binder) should be added to the granulation mixture, especially when the granulate should contain a relatively large amount of active principle. Further information on this can be found e.g. in H. A. Lieberman and L. Lachran, Pharmaceutical Dosage Forms (1980), Vol. I, pp 113-116 ("Wet granulation") or in L. Lachman, H. A. Lieberman and J. L. Kanig, The Theory and Practice of Industrial Pharmacy, 3rd Ed., pp 320-324 ("Wet Granulation"). Examples of wet binders are acacia gum, gelatin, polyvinylpyrrolidone, starch (paste and pre-gelatinized), sodium alginate and alginate derivatives, sorbitol, glucose and other sugars, tragacanth and soluble celluloses like methylcellulose, hydroxypropylmethylcellulose, sodium carboxymethylcellulose and hydroxypropylcellulose. Wet binders are usually applied in a granulation mixture in amounts of 1-10 wt % with respect to the active principle. Although the use of a wet binding substance for granulation is considered necessary to obtain a good granulate, it has appeared that tablets prepared from such granulates show a poor disintegration behaviour when immersed in water. This may be a disadvantage from the biological absorption viewpoint. The therapeutically useful substance is released from fast disintegrating tablets in a very short time, with the effect that the absorption and the therapeutic action begins earlier and higher initial drug concentrations in the body are attained.

The aim of the present invention is to provide a good quality granulate which, although containing a relatively large amount of active substance, may be further processed to solid tablets having a satisfactory disintegration behaviour.

SUMMARY OF THE INVENTION

It has now surprisingly been found that, by the use of wet granulation, a good quality granulate can be made from a therapeutically useful substance, present in high concentrations, but having limited solubility in water of less than 10 wt %, together with a cellulose product which can be microcrystalline cellulose or microfine cellulose or a mixture of both, but without the addition of a substantial amount of a wet binding substance. The granulate of the invention passes uninterruptedly flow cup orifices not wider than 12 mm and often even less.

DETAILS OF THE INVENTION

In order to obtain the new granulate, use is made of the wet granulation processes which are well known in the art. The invention can be used with many kinds of therapeutically useful substances, such as beta-lactam antibiotics, tetracyclines, steroids, etc., provided that their solubility in water is less than 10 wt % and preferably less than 5 wt %. For example the following therapeutically useful substances may be successfully granulated according to the present invention: amiodarone, amoxicillin, cimetidine, chloramphenicol, cotrimoxazol, doxycycline monohydrate, erythromycine ethyl succinate, flumequine, furazolidone, hydrotalcite, ibuprofen, indomethacin, L-dopa, naproxen, paracetamol, penicillin-V acid, pipemidic acid, piroxicam, progesterone, proligestone, oxytetracycline dihydrate, sulfamethoxazole, sulindac, spironolactone, theophylline and trimethoprim.

The granulation mixture is preferably prepared by first mixing the active principle with microcrystalline cellulose or microfine cellulose or a mixture of both. Microcrystalline cellulose is the common name for purified, partially depolymerized cellulose occurring as a crystalline powder, comprising porous particles. It is a widely used adjuvant, known e.g. under the brand name AVICEL. Some AVICEL grades, particularly AVICEL RC-581, contain the wet binder sodium carboxymethylcellulose in an amount of about 11 wt %. But according to the present invention only microcrystalline cellulose with less than 10 wt %, if any wet binder (preferably AVICEL PH-102) is used. Microfine cellulose, e.g. ELCEMA TM, also known as powdered cellulose, is a mechanically processed alpha-cellulose derived from fibrous plant materials. It is a common pharmaceutical binder and disintegrant. In this description and the appended claims "cellulose product" refers particularly to microcrystalline cellulose and microfinecellulose and to mixtures of them. The cellulose product may be employed in amounts of 20-100 wt %, preferably 35-45 wt % based on the weight of the therapeutically useful substance.

Various granulation liquids are known and may be used, e.g. methylene chloride and isopropyl alcohol, but preferably water is used. The amount of granulation liquid may be 40-135 wt %, preferably 60-90 wt %, based on the weight of the therapeutically useful substance.

The use of a wet binding substance, such as those described above, in the granulation mixture should be avoided or at least restricted to an amount of not more than 0.5 wt %, preferably to less than 0.1 wt % based on the weight of the therapeutically active substance. Otherwise the disintegration behaviour of the tablets prepared from the granulate is adversely affected.

Whereas many of the above-mentioned therapeutically useful substances have unsatisfactory flow properties, resulting in tableting mixtures which are hard to process, the new granulate and the mixtures made with the new granulate have a substantially improved flow pattern. According to a standard test, still to be described, the narrowest flow cup orifice through which the powder can uninterruptedly flow is not wider than 12 mm. and often even less.

The invention granulate as such disperses rapidly in water. Also tablets made from the granulate and, optionally, one or more adjuvants, show a very good disintegration behaviour when immersed in water of about 20° C., normally resulting within 60 seconds in an excellent suspension which is free of coarse lumps.

The flow behaviour of the granulates according to the invention and of the tableting mixtures containing those granulates can be quantified by using as parameter the orifice diameter of a funnel like cup, denoted as flow cup, through which the powder appears to flow uninterruptedly. If a powder can flow uninterruptedly through an orifice of 2.5 mm its flow behaviour is rated "excellent".

The cylindrical glass flow cups have a length of about 65 mm, and a diameter of about 39 mm. The bottom is conically shaped with a central round orifice. The silicone lined cups are partially (about half) filled with powder. The test procedure allows to start the powder running by tapping at the flow-cup, but after that the powder should uninterruptedly flow out of the cup till empty. The applied ratings are:

| Cup number | Orifice | Behaviour |
|---|---|---|
| 1 | 2.5 mm | excellent |
| 2 | 5.0 mm | good |
| 3 | 8.0 mm | fair |
| 4 | 12.0 mm | passable |
| 5 | 18.0 mm | poor |
| 6 | — | very poor |

The invention is further illustrated by the following examples, which should however not be construed as a limitation of the invention.

All percentages, unless otherwise indicated, are based on the weight of the therapeutically active substance.

The indicated dispersion times refer to tablets made with the granulate according to the formulation of Example 28 and using water of about 20° C. for disintegration. cps means centipoise low-substituted hydroxypropylcellulose is denoted by LH 11 or 1-HPC.

EXAMPLES 1-27

The pharmaceutical substances according to the following tables were mixed with either 40 wt % (Table 1), or 100 wt % (Table 2) microcrystalline cellulose (AVICEL PH-102) and the amount of water as mentioned in Tables 1 and 2. The resulting wet mass was sieved through a 2 mm mesh sieve and dried in a fluidized bed dryer at about 60° C. for about one hour. The resulting dry granulate was sieved through a 0.8 mm mesh sieve and collected.

TABLE 1

| Example | Therapeutically useful compound with 40 wt % AVICEL PH-102 | Gran. liq. wt % | Tableting mixture flow orifice (mm) | Granulate flow orifice (mm) | Tablet dispersion* time (sec) |
|---|---|---|---|---|---|
| 1 | amiodarone | 64 | 5 | 5 | 45 |
| 2 | amoxicillin | 64 | 5 | 5 | 50 |
| 3 | cimetidine | 70 | 5 | 5 | 25 |
| 4 | chloramphenicol | 77 | 5 | 5 | 25 |
| 5 | cotrimoxazol | 64 | 8 | 12 | 25 |
| 6 | doxycycline monohydrate | 64 | 2 | 2 | 20 |
| 7 | flumequine | 75 | 2 | 2 | 25 |
| 8 | furazolidone | 64 | 5 | 5 | 30 |
| 9 | hydrotalcite | 118 | 5 | 5 | 10 |
| 10 | ibuprofen | 84 | 5 | 12 | 40 |
| 11 | indomethacin | 81 | 5 | 5 | 25 |
| 12 | L-dopa | 84 | 5 | 5 | 20 |
| 13 | paracetamol | 91 | 5 | 5 | 25 |
| 14 | penicillin-V ac | 64 | 2 | 2 | 20 |
| 15 | pipemidic acid | 77 | 5 | 5 | 20 |
| 16 | piroxicam | 84 | 5 | 8 | 20 |
| 17 | progesterone | 65 | 5 | 5 | 40 |
| 18 | proligestone | 71 | 2 | 2 | 25 |
| 19 | oxytetracycline dihydrate | 64 | 2 | 2 | 35 |
| 20 | sulfamethoxazol | 71 | 5 | 12 | 20 |
| 21 | sulindac | 94 | 5 | 5 | 20 |
| 22 | spironolactone | 70 | 2 | 2 | 20 |
| 23 | theophylline | 64 | 2 | 2 | 20 |

*in water of about 20° C.

TABLE 2

| Example | Therapeutically useful compound with 100 wt % AVICEL PH-102 | Gran. liquid wt % | Tableting mixture flow orifice (mm) | Granulate flow orifice (mm) | Tablet dispersion time* (sec) |
|---|---|---|---|---|---|
| 24 | erythromycine ethyl succinate | 133 | 8 | 12 | 50 |
| 25 | naproxen | 133 | 5 | 5 | 25 |
| 26 | piroxicam | 110 | 5 | 5 | 20 |
| 27 | trimethoprim | 133 | 8 | 12 | 30 |

*in water of about 20° C.

EXAMPLE 28

The granulates obtained according to the previous examples were used to press tablets in the usual way using the following mixture

| 90.25 g | granulate |
| 1.45 g | microcrystalline cellulose |
| 5.34 g | low-substituted hydroxypropylcellulose |
| 2.00 g | flavours |
| 0.16 g | colloidal silica gel |
| 0.80 g | magnesium stearate |

Each tableting mixture was passed through the flow cups of the test to determine the smallest flow cup orifice through which each mixture could still uninterruptedly flow. The results are set out in the above Tables 1 and 2.

The resulting 15 mm tablets had a hardness of 100-150 N and a disintegration time as shown in the above Tables 1 and 2. This time was assessed employing the usual USP disintegration tester (ERWEKA).

EXAMPLE 29

200 g of amoxicillin trihydrate were mixed with 80 g of microfine cellulose (ELCEMA G400) and 150 ml of water. The resulting wet mass was kneaded for 20 minutes, sieved through a 2 mm mesh sieve and dried in a fluidized bed drier at about 60° C. for about one hour until the granulate contained not more than 10.5 wt % of water. The resulting dry granulate was sieved through a 0.8 mm sieve and collected.

EXAMPLE 30

| | |
|---|---|
| 50 g | granulate from Example 29 |
| 3.09 g | microfine cellulose (ELCEMA G400) |
| 3.09 g | 1-HPC |
| 0.1 g | colloidal silica gel |
| 0.56 g | saccharin |
| 0.62 g | flavours |
| 0.47 g | magnesium stearate |

The granulate was mixed for 10 minutes with the other excipients, after which the resulting mixture was compressed into tablets on a rotary press. The prepared 960 mg tablets had a hardness of 106N and disintegrated in water of 20° C. within 40 seconds.

EXAMPLE 31

| | |
|---|---|
| 100 g | amoxicillin containing granulate from Example 2 |
| 6.18 g | microcrystalline cellulose (AVICEL PH-102) |
| 6.18 g | cross-linked polyvinylpyrrolidon (KOLLIDON CL) |
| 0.19 g | colloidal silica gel |
| 0.93 g | magnesium stearate |

Following the procedure of Example 30, 955 mg tablets were obtained having a hardness of 107N and a disintegration time of 26 seconds in water of 20° C.

EXAMPLE 32

Doxycycline monohydrate (105.8 g) and microcrystalline cellulose (AVICEL PH-102) (45 g) were mixed for 15 minutes in a planetary mixer. The mixture was granulated with 60 ml of water. After 10 minutes of kneading the resulting wet mass was passed through a 2 mm sieve and the wet granulation dried at about 40° C. until its water content was below 2%. The granulation was passed through a 0.71 mm sieve and mixed for 20 minutes with low-substituted hydroxypropylcellulose LHII (18 g), hydroxypropyl methylcellulose 5 cps (4 g), saccharin (10 g), colloidal silica gel (0.6 g) and enough lactose to bring the total weight on 248 g. Then magnesium stearate (2 g) was added and the mixing was continued for an additional 2 minutes. The resulting mixture was compressed into tablets of about 250 mg, about 9 mm diameter and a hardness of 68-97N or into tablets of about 125 mg having a hardness of 58-87 N. They disintegrated completely in water of 20° C. within 30-45 sec.

EXAMPLES 33-36

The pharmaceutical substances according to Table 3 were mixed with 40 wt % of microcrystalline cellulose (AVICEL PH-102) and 0.1 wt % of polyvinyl pyrrolidone (PVP K30, mean molecular weight 49000). The resulting mixture was granulated by mixing with the amount of water mentioned in Table 3. The resulting mass was passed through a 2 mm sieve and then dried overnight at 60° C. The dried mass was passed through a 0.8 mm sieve and collected.

TABLE 3

| Example | Therap. useful comp. | Water wt % | Tablet mixt. flow or. (mm) | Granulate flow orifice (mm) | Tablet disper sion* (sec) |
|---|---|---|---|---|---|
| 33 | Sulfamethoxazole | 77 | 8 | 12 | 43 |
| 34 | Trimethoprim | 84 | 5 | 8 | 40 |
| 35 | Co-trimoxazole | 77 | 5 | 5 | 30 |
| 36 | Ibuprofen | 98 | 5 | 5 | 30 |

*in water of about 20° C.

EXAMPLE 37

The granulates obtained according to examples 33-36 were used to press tablets using the following mixture:

| | |
|---|---|
| 45.13 g | granulate |
| 0.63 g | microcrystalline cellulose |
| 2.67 g | low-substituted hydroxypropylcellulose |
| 1.00 g | flavours |
| 0.08 g | colloidal silica gel |
| 0.40 g | magnesium stearate. |

With flow cups the flow properties of each tableting mixture were determined. The smallest orifice through which each mixture could uninterruptedly flow can be found in Table 3. Tablets of 1130 mg were pressed with a diameter of 15 mm and a hardness of 100-150N. The disintegration times in water of 20° C. were measured using the USP disintegration tester (ERWEKA). The results are set out in Table 3.

EXAMPLE 38

7.145 of erythromycine ethyl succinate was mixed with 0.0071 g of PVP K30 and 2.86 g of microcrystalline cellulose. The mixture was wet granulated using 5 ml of isopropyl alcohol. The resulting granulate was passed through a 2 mm sieve and then dried overnight at 60° C. The dried granulate, after passing through a 0.8 mm sieve, flowed uninterruptedly through a flow cup with an orifice of 8 mm. 9 g of the granulate was mixed with:

| | |
|---|---|
| 145 mg | of microcrystalline cellulose |
| 530 mg | of low-substituted hydroxypropylcellulose |
| 200 mg | of flavours |
| 16 mg | of colloidal silica gel |
| 80 mg | of magnesium stearate. |

The resulting tabletting mixture flowed uninterruptedly through an orifice of 5 mm.

Tablets of 1130 mg (having a diameter of 15 mm) were pressed with a hardness of 100-150N. The disintegration time of the tablets in water of 20° C. was 40-50 seconds.

We claim:
1. A process for the preparation of a pharmaceutical granulate, which can uninterruptedly flow through a flow cup orifice not wider than 12 mm, and after placing it in water, readily results in a smooth dispersion, free of coarse lumps, comprising the steps of:
mixing a therapeutically useful substance having a solubility in water of less than 10 wt %, a cellulose product selected from the group consisting of microcrystalline cellulose, microfine cellulose and mixtures thereof, and 0-0.5 wt % of a wet binder substance based on the weight of said therapeutically useful substance with water to form a wet mass;

processing said wet mass to form a granulate;

passing said wet mass through a first woven wire screen;

drying the sieved granulate;

passing the dried granulate through a second woven wire screen; and collecting the resulting granulate.

2. The process according to claim 1, wherein said therapeutically useful substance comprises at least 50 wt % of the granulate.

3. The process according to claim 1, wherein said granulate contains 0-0.1 wt % of a wet binding substance based on the weight of said therapeutically useful substance.

4. The process according to claim 1, wherein said therapeutically useful substance has a solubility in water of less than 5 wt %.

5. The process according to claim 1, wherein said granulate contains 20-100 wt % of said cellulose product based on the weight of said therapeutically useful substance.

6. The process of claim 1, wherein said therapeutically useful substance is an amphoteric beta-lactum antibiotic.

7. The process of claim 1, wherein said therapeutically useful substance is a tetracycline antibiotic.

8. The process of claim 1, wherein said therapeutically useful substance is hydrotalcite.

9. The process of claim 1, wherein said granulate contains 35-45 wt % of said cellulose product based on the weight of said therapeutically useful substance.

10. The process of claim 1, further comprising the step of pressing the resultant granulate into tablets.

11. The process of claim 1, wherein the first mesh sieve is a 2 mm mesh sieve.

12. The process of claim 1, wherein the sieved granulate is dried at temperature of about 60° C. for about one hour.

13. The process of claim 1, wherein the second sieve is a 0.8 mm mesh sieve.

14. The process of claim 1, wherein the amount of water used is 40-135 wt % based on the weight of said therapeutically useful substance.

15. The process of claim 1, wherein the amount of water used is 60-90 wt % based on the weight of said therapeutically useful substance.

* * * * *